(12) United States Patent
Polaire

(10) Patent No.: US 6,721,962 B1
(45) Date of Patent: Apr. 20, 2004

(54) HAT WITH BRIM LIGHT

(76) Inventor: Michael Polaire, P.O. Box 5010, Larkspur, CA (US) 94977-5010

( * ) Notice: Subject to any disclaimer, the term of this patent is extended or adjusted under 35 U.S.C. 154(b) by 0 days.

(21) Appl. No.: 10/369,248

(22) Filed: Feb. 19, 2003

(51) Int. Cl.[7] ................................................ A42B 1/24
(52) U.S. Cl. ........................... 2/209.13; 2/906; 362/105
(58) Field of Search .................. 2/209.13, 175.1–175.4, 2/195.1–195.5, 905, 906; 362/103, 105, 106

(56) References Cited

U.S. PATENT DOCUMENTS

| | | | |
|---|---|---|---|
| 1,146,979 A | | 7/1915 | Walters et al. |
| 4,525,878 A | * | 7/1985 | Lowe, Jr. .................... 2/209.13 |
| 4,551,857 A | * | 11/1985 | Galvin ............................... 2/7 |
| 4,901,211 A | | 2/1990 | Shen |
| 4,991,068 A | * | 2/1991 | Mickey ...................... 362/106 |
| 5,088,127 A | * | 2/1992 | Thornock .................. 2/209.13 |
| 5,404,593 A | * | 4/1995 | Kronenberger ............. 2/195.1 |
| 5,510,961 A | * | 4/1996 | Peng ........................... 362/106 |
| 5,541,816 A | | 7/1996 | Miserendino |
| 5,680,718 A | * | 10/1997 | Ratcliffe et al. .............. 40/329 |
| 5,741,060 A | | 4/1998 | Johnson |
| 5,743,621 A | * | 4/1998 | Mantha et al. .............. 362/105 |
| 6,032,291 A | * | 3/2000 | Asenguah et al. ........... 2/171.3 |
| 6,032,293 A | * | 3/2000 | Makki ....................... 2/209.13 |
| 6,168,286 B1 | | 1/2001 | Duffy |
| 6,244,721 B1 | * | 6/2001 | Rodriguez et al. .......... 362/106 |

* cited by examiner

*Primary Examiner*—Katherine Moran
(74) *Attorney, Agent, or Firm*—Brown Raysman Millstein Felder & Steiner LLP

(57) ABSTRACT

A lighted hat 10 provides illumination for the user of the hat while substantially maintaining the appearance of a traditional baseball style cap visor. The lighted hat 10 includes a head-engaging portion 20, a brim 30, a headband 40, a low profile light 50, a power source 60, and an activation switch 80. A preferred embodiment lighted hat 10 is configured as a traditional baseball style cap that has a head-engaging portion 20 and a brim 30 attached to the front of the head-engaging portion. Additionally, a headband 40 is also preferably connected to the lower inside rim of the head-engaging portion 20. The low profile light 50 is incorporated into the brim 30 of the hat 10 where it is substantially concealed within the brim. In one embodiment, the power source 60 includes a solar panel 70 that is located on the brim 30 of the hat 10.

26 Claims, 5 Drawing Sheets

HAT WITH BRIM LIGHT

FIELD OF THE INVENTION

This invention relates generally to a hat having a light and, more particularly, to a hat having a light incorporated into the brim of the hat, whereby the appearance of a standard hat having no light is maintained.

BACKGROUND OF THE INVENTION

Various types of portable lights are known in the art. In this regard, the concept of attaching lighting devices to hats is also known. For example, the common miner's hat made use of a carbide lamp attached to a hat for working in mineral mines, as well as for cave exploration. Various other types of head-lights also have been produced, most of which are spotlights. Such lights are frequently attached to hard hats and various other devices that encircle the head in a band-like fashion. These lights generally have a flashlight-type beam and, sometimes, a focusing lens.

These types of lighted hats have a number of disadvantages. One prior lighted headpiece basically consists of a flashlight that is attached to the side of the head. This device has the disadvantage of requiring the user to view the object of interest out of the corner of the user's eye. Additionally, this device utilizes Velcro® attachments, thereby making it difficult to adjust the direction of the light in a vertical plane. Further, the weight of the hat can cause discomfort to the user.

Other known lighting devices are mounted on the forehead of the user with some type of strap. These devices are unsightly because they are dramatically different from anything a person would normally wear upon his head. Still other known devices are mounted on top of the head with a helmet. Again, these lighted hats are unsightly.

Moreover, these lighted hats tend to be too heavy and bulky for many uses. Accordingly, these lighted hats are typically not very aesthetically appealing and are uncomfortable to many potential users, especially those who do not necessarily want to make known that they are wearing a hat with a light. Thus, those skilled in the art have recognized the need for a hat that has the advantages provided by having a light integrated therein, but yet overcomes many of the drawbacks of prior lighted hats. The present invention clearly addresses these and other needs.

SUMMARY OF THE INVENTION

Briefly, and in general terms, the present invention resolves the above and other problems by providing a hat having a light to produce illumination for a user of the hat while still maintaining the aesthetics and comfort of a non-lighted hat. In accordance with the present invention, the hat includes a head-engaging portion, a brim, a low profile light, a power source, and an activation switch. The brim is attached to the head-engaging portion of the hat. Preferably, the head-engaging portion further includes a headband at the lower edge of the head-engaging portion. The low profile light is incorporated into the brim of the hat where it is substantially concealed within the brim. The power source is connected to the hat and is operatively associated with the light by connective wiring. The activation switch is connected to the hat and is used for activating and deactivating the light. The activation switch is operatively associated with the light and the power source by connective wiring.

More particularly, in one embodiment the power source is a battery that is substantially concealed in the headband of the hat. In another embodiment, the battery is used in conjunction with a solar panel that is preferably located upon the brim of the hat. In one embodiment that implements solar power, a photovoltaic gel battery is utilized.

In accordance with one aspect of the present invention, the light is directionally configured within the brim of the hat to illuminate a user's line of sight. Additionally, the activation switch is substantially concealed within the brim of the hat. Locating the activation switch within the brim of the hat facilitates ease of activation and deactivation by the user of the hat while still maintaining the appearance of a standard, non-lighted hat. Preferably, the activation switch is a push-button type switch. Other types of switches may, of course, be used.

In accordance with another aspect of the present invention, the hat has the appearance of an ordinary non-lighted hat due to the substantial concealment of the light within the brim. Preferably, the low profile light has a translucent plastic lens. In one preferred embodiment, by way of example and not necessarily by way of limitation, the low profile light is approximately three inches in length across the brim's front edge.

Another preferred embodiment of the present invention is directed towards a cap having a traditional baseball style cap. The cap has a light source incorporated into the traditional baseball style cap so as to substantially maintain the traditional baseball cap-type shape and feel. In this preferred embodiment, the cap includes a head-engaging portion, a brim, a low profile light substantially concealed within the brim, a power source, and an activation switch.

Yet another preferred embodiment of the present invention is directed towards a visor having a traditional tennis visor shape. The visor also has a light source incorporated into the traditional tennis visor so as to substantially maintain the traditional tennis visor shape and feel. Preferably, the visor includes substantially the same components as the other hat and cap embodiments; however, the head-engaging portion of the visor typically covers less of the crown of the wearer's head than the other embodiments of the present invention.

Other features and advantages of the present invention will become apparent from the following detailed description, taken in conjunction with the accompanying drawings, which illustrate by way of example, the features of the present invention.

DETAILED DESCRIPTION OF THE PREFERRED EMBODIMENTS

In general, the present invention allows the incorporation of a light within the brim of a hat, cap, or visor so as to illuminate the user's line of sight while still maintaining the aesthetics and feel of a non-lighted hat, cap, or visor.

More particularly, a preferred embodiment lighted hat 10, constructed in accordance with the present invention, provides illumination for the user of the hat while substantially maintaining the appearance of a traditional baseball style cap. The lighted hat 10 covertly incorporates a light and a power source into the hat so as to preserve the shape and comfort of a traditional baseball style cap that does not contain a light source. In this manner, an individual may wear a lighted hat 10 that maintains the characteristics and appearance of an unlighted hat.

Figure 1:
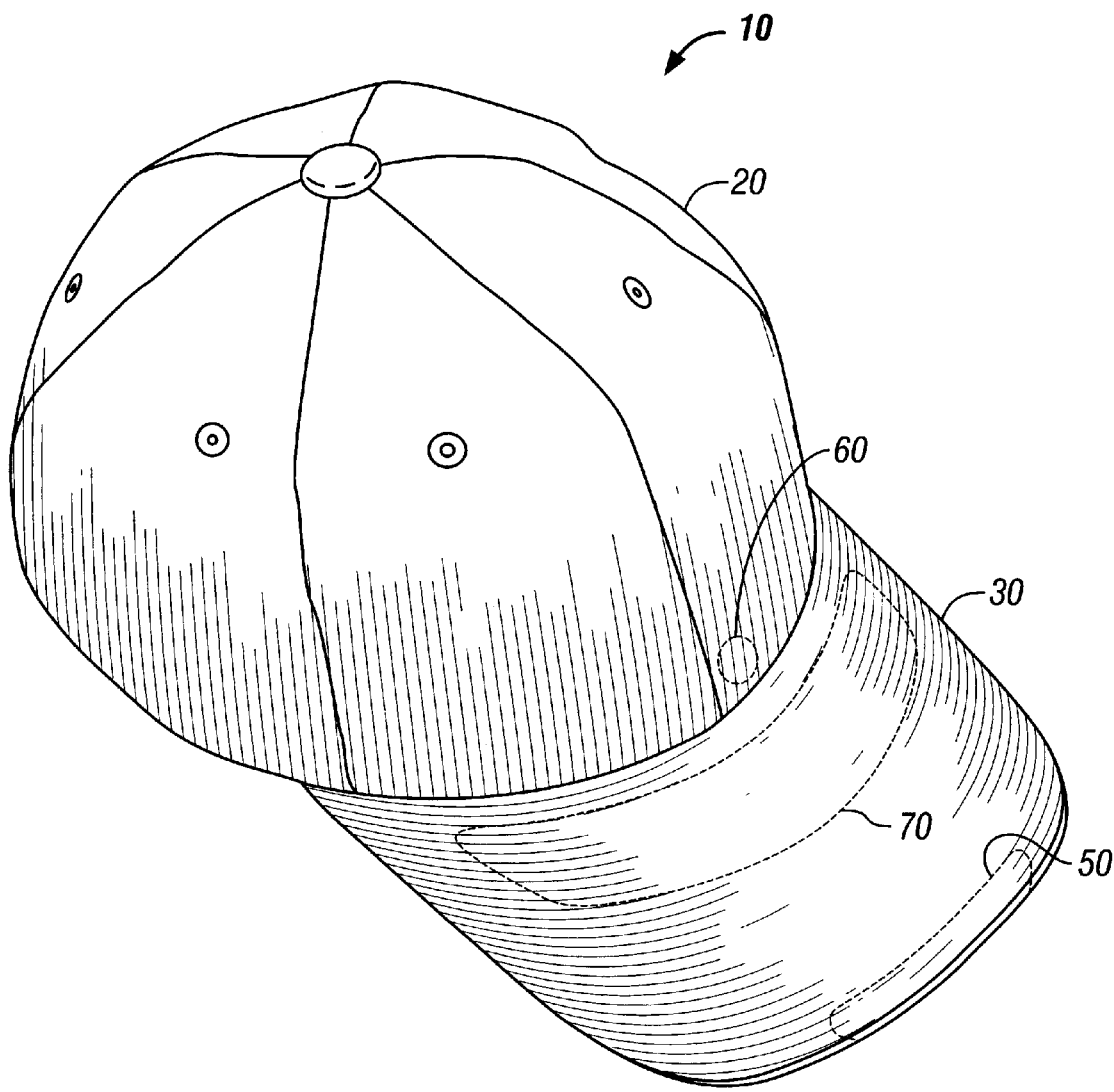
FIG. 1 illustrates a perspective view of a preferred embodiment hat having a light located within the brim, in accordance with the present invention.
Figure 2:
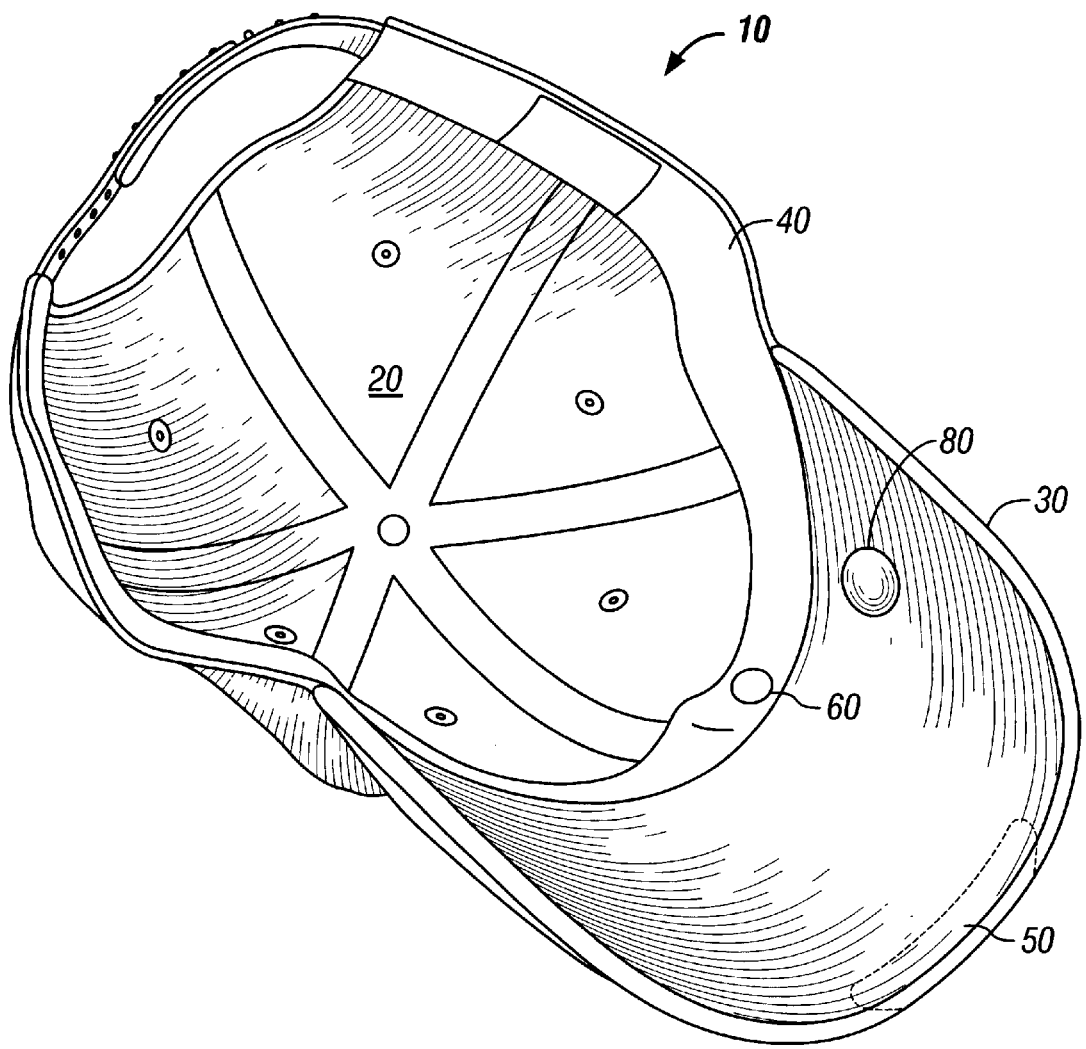
FIG. 2 illustrates a bottom perspective view of a preferred embodiment hat having a light located within the brim, in accordance with the present invention.

Referring now to the drawings, wherein like reference numerals denote like or corresponding parts throughout the drawings and, more particularly to FIGS. 1–2, there is shown one embodiment of a lighted hat 10 constructed in accordance with the present invention. Briefly stated, the lighted hat 10 includes a head-engaging portion 20, a brim 30, a headband 40, a light 50, a power source 60, and an activation switch 70. A preferred embodiment lighted hat 10 is configured as a traditional baseball style cap that has a head-engaging portion 20 and a brim 30 attached to the front of the head-engaging portion. Additionally, a headband 40 also preferably is connected to the lower inside rim of the head-engaging portion 20, as in a traditional baseball cap. Further, in some preferred embodiments of the present invention, the rear of the head-engaging portion 20 includes an adjustment band for adjusting the fit of the hat 10 to the user's head size.

In a preferred embodiment of the present invention, the light 50 is configured to have a low profile in order to facilitate incorporation of the light into the brim 30 of the hat 10. In this manner, the low profile light 50 is substantially concealed within the brim 30, and, therefore, the hat 10 is able to maintain the appearance of a traditional non-lighted baseball cap. Preferably, the light 50 also is either sufficiently flexible, curved, or narrow so that the brim 30 of the hat 10 is able to maintain the traditional curved appearance of a typical baseball cap brim. In one preferred embodiment, the light 50 is directionally positioned within the brim 30 of the hat 10 to illuminate the user's line of sight. Thus, by virtue of the user's head movements, the hat 10 can maintain the focus and direction of the light 50 within the user's line of sight. Preferably, the low profile light 50 has a translucent plastic lens that is sufficiently durable to withstand the normal wear and tear typically experienced by a normal baseball cap. In one preferred embodiment, the low profile light 50 is approximately three inches in length across the brim's front edge. Of course, one of ordinary skill in the art will appreciate that other length lens may be used without departing from the scope of the present invention.

As previously stated, a power source 60 is concealed within the lighted hat 10 in such a manner so as to maintain the appearance of a traditional baseball style cap. More particularly, in one preferred embodiment of the present invention, the power source 60 is a battery and is substantially concealed within the headband 40 of the hat 10. In other embodiments, the battery 60 is located in various, other positions within the hat 10, such as the brim 30, but in a manner to maintain substantial concealment of the battery. A wide variety of batteries may be used to power the lighted hat 10; however, preferably the battery 60 selected is of a diminutive size in order to allow for ease of concealment. Furthermore, a battery having long life is also preferred, but not required, in accordance with the present invention.

In a preferred embodiment, the battery 60 is positioned for substantial accessibility so that the battery can be easily replaced when necessary. Further, the battery 60 is connected to the light 50 by way of connective wiring that enables the battery to power the light. Preferably, the battery 60 is positioned in a location that minimizes the distance between the battery and the light 50, and thus, minimizes the length of connective wiring that is required. It is desirable to minimize the amount of connective wiring utilized to avoid the wire from shorting out as a result of extensive wear and tear. It is understood that the connective wiring is also placed so as to conceal its presence within the hat.

In another embodiment, the power source includes a solar panel 70. The solar panel 70 is preferably located up on the brim 30 of the lighted hat 10. Since baseball style caps are often worn to provide shade from sunlight, a solar powered embodiment of the lighted hat 10 would be able to charge a solar battery cell during the day, and then use that energy at night to power the light 50 located within the brim 30 of the hat. In one preferred embodiment of the present invention that implements solar power, a photo voltaic gel battery is utilized. It will be appreciated that other solar powered systems may be utilized in accordance with the present invention.

In a preferred embodiment, the activation switch 80 is substantially concealed within the brim 30 of the hat 10. Specifically, in one preferred embodiment of the present invention, the activation switch 80 is located on the lower right-hand side of the brim 30. This location is ergonomically appealing, since it is the location where a user would normally grasp the hat 10 in order to place it upon or to remove it from the user's head. While the activation switch may be located within various other locations of the lighted hat 10 without departing from the scope of the present invention, locating the activation switch in the brim 30 of the hat facilitates ease of activation and deactivation by the user of the hat. Preferably, the activation switch 80 is a push button type switch that the user can easily squeeze to activate and deactivate the light 50. However, any appropriate switch may be used.

Additionally, the activation switch 80 is connected to both the battery 60 and the light 50 by way of connective wiring that enables the activation switch to regulate whether or not the battery provides power to the light. Preferably, the activation switch 80 is positioned in a location that minimizes the distance between the activation switch, the battery 60, and the light 50, and thus, minimizes the amount of connective wiring that is required. As described above, it is desirable to minimize the amount of connective wiring utilized to avoid a potential shorting of the wire after extensive wear and tear.

Figure 3:
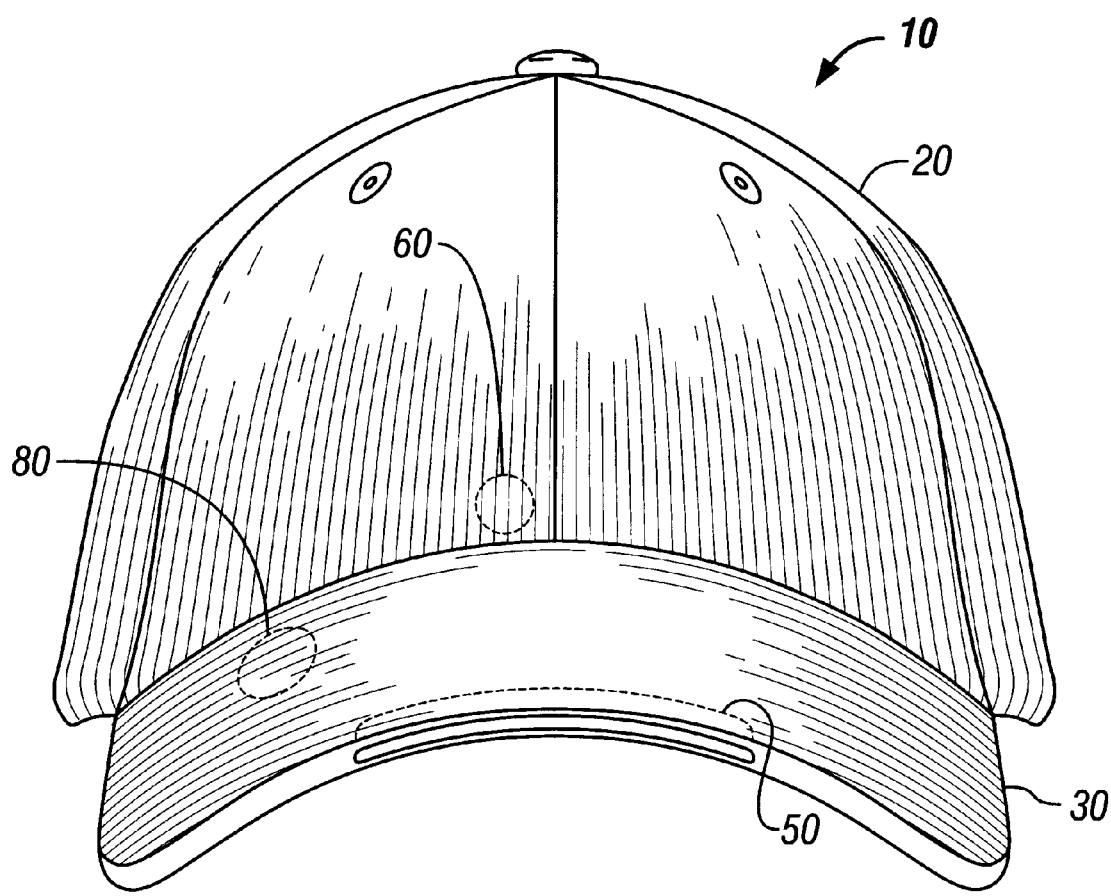
FIG. 3 illustrates a front view of a preferred embodiment hat having a light located within the brim, in accordance with the present invention.
Figure 4:
FIG. 4 illustrates a side view of a preferred embodiment hat having a light located within the brim, wherein the preferred embodiment hat is situated on a user's head.

FIGS. 3 and 4 illustrate a preferred embodiment lighted hat 10 viewed from additional directions. FIG. 3 shows the lighted hat 10 from a frontal view, and demonstrates how the lighted hat of the present invention is virtually indistinguishable in appearance from a standard hat having no light in the brim. Specifically, FIG. 3 illustrates how only the leading edge of the low profile light 50 is visible in the brim of the hat 10 when viewed directly from the front. Moreover, FIG. 4 shows the lighted hat 10 of the present invention from a side view while being worn by an individual and used by that individual to provide desired illumination.

Figure 5:
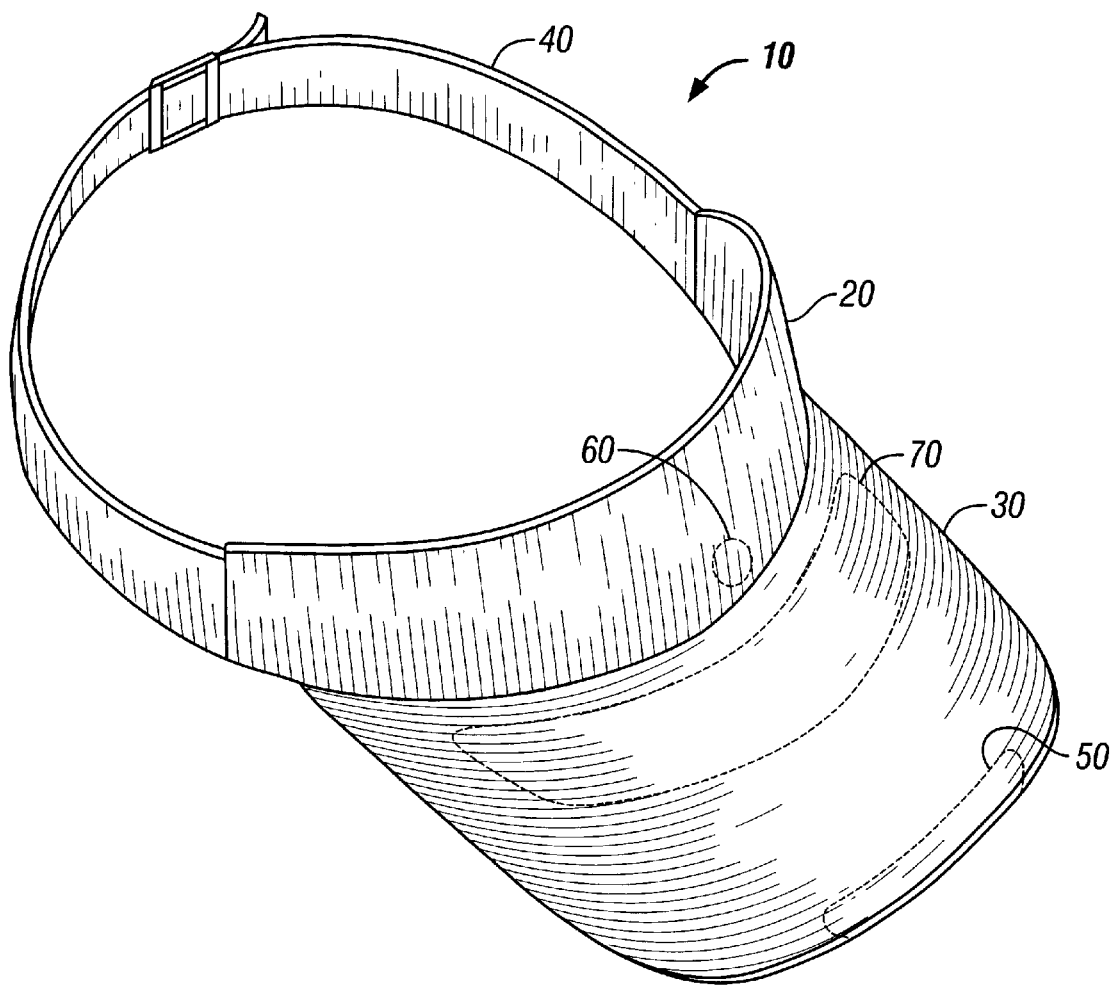
FIG. 5 illustrates a perspective view of a preferred embodiment visor having a light located within the brim, in accordance with the present invention.

As shown in FIG. 5, another preferred embodiment lighted hat 10, constructed in accordance with the present invention, provides illumination for the user of the hat while substantially maintaining the appearance of a traditional tennis visor. The visor also has an incorporated light source so as to substantially maintain the traditional tennis visor shape and feel. Preferably, the visor includes substantially the same components as the other hat and cap embodiments; however, the head-engaging portion of the visor typically covers less of the crown of the wearer's head than the other embodiments of the present invention.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

What is claimed is:

1. A hat having a light that provides illumination for a user of the hat, the hat comprising:
   a head-engaging portion and a brim attached thereto;
   a single, non-circular low profile light incorporated into the brim, wherein the light is substantially concealed within the brim of the hat, and wherein the light extends longitudinally along a portion of a front edge of the brim;
   a power source operatively associated with the light; and
   an activation switch for activating and deactivating the light, wherein the activation switch is operatively associated with the light and the power source.

2. The hat of claim 1, wherein the head-engaging portion further includes a headband, and wherein the power source includes a battery that is substantially concealed within the headband of the hat.

3. The hat of claim 1, wherein the power source includes a battery, and is used in conjunction with a solar panel located on the brim of the hat.

4. The hat of claim 3, wherein the battery comprises a photovoltaic gel battery.

5. The hat of claim 1, wherein the light is directionally configured within the brim of the hat to illuminate the user's line of sight.

6. The hat of claim 1, wherein the activation switch is a push button type switch.

7. The hat of claim 1, wherein the activation switch is substantially concealed within the brim of the hat to facilitate ease of activation and deactivation.

8. The hat of claim 1, wherein the hat has the appearance of an ordinary non-lighted baseball style cap due to the substantial concealment of the light within the brim.

9. A baseball cap having a light that provides illumination for a user of the cap, the baseball cap having a light and a power source covertly incorporated into the baseball cap so as to substantially maintain a traditional baseball style cap shape, the cap comprising:
   a head-engaging portion and a brier attached thereto;
   a non-circular low profile light incorporated into the brim, wherein the light is substantially concealed within the brim of the cap, and wherein the light is sufficiently curved to allow the brim to maintain the appearance of a traditional curved baseball cap brim;
   a power source operatively associated with the light; and
   an activation switch for activating and deactivating the light, wherein the activation switch is operatively associated with the light and the power source.

10. The cap of claim 9, wherein the head-engaging portion of the cap includes a headband, and wherein the battery is substantially concealed within the headband of the hat.

11. The cap of claim 9, wherein the battery is used in conjunction with a solar panel located on the brim of the cap.

12. The cap of claim 11, wherein the battery comprises a photovoltaic gel battery.

13. The cap of claim 9, wherein the light source is directionally configured within the brim of the cap to illuminate a user's line of sight.

14. The cap of claim 9, herein the activation switch is a push button type switch.

15. The cap of claim 9, wherein the activation switch is substantially concealed within the brim of the cap to facilitate ease of activation and deactivation.

16. The cap of claim 9, wherein the light, battery, and activation switch are substantially concealed within the cap, thereby assisting in maintaining the substantial appearance of m non-lighted baseball style cap.

17. The cap of claim 9, wherein the light incorporated into the brim is sufficiently flexible to allow the brim to maintain the appearance of a traditional curved baseball cap brim.

18. The cap of claim 9, wherein the light incorporated into the brim is sufficiently narrow to allow the brim to maintain the appearance of a traditional curved baseball cap brim.

19. A visor having a traditional tennis visor shape, the visor having a light source incorporated into the traditional tennis visor style so as to substantially maintain the traditional tennis visor shape, the visor comprising:
   a head-engaging portion and a brim attached thereto;
   a non-circular low profile light substantially concealed within the brim, and wherein the light is sufficiently curved to allow the brim to maintain the appearance of a traditional curved visor brim;
   a power source operatively associated with the light; and
   an activation switch operatively associated with the light, wherein said switch activates and deactivate the light.

20. The visor of claim 19, wherein the power source is substantially concealed within the visor.

21. The visor of claim 19, wherein the power source is used in conjunction with a solar panel located on the brim of the visor.

22. The visor of claim 19, wherein the power source comprises a photovoltaic gel battery.

23. The visor of claim 19, wherein the light source is directionally configured within the brim of the visor to illuminate a user's line of sight.

24. The visor of claim 19, wherein the activation switch is a push button type switch.

25. The visor of claim 19, wherein the activation switch is substantially concealed within the brim of the visor to facilitate ease of activation and deactivation.

26. The visor of claim 19, wherein the visor maintains the appearance of a non-lighted tennis visor due to the substantial concealment of the light, battery, and activation switch located within the visor.

* * * * *

UNITED STATES PATENT AND TRADEMARK OFFICE
CERTIFICATE OF CORRECTION

PATENT NO. : 6,721,962 B1 Page 1 of 1
DATED : April 20, 2004
INVENTOR(S) : Michael Polaire It is certified that error appears in the above-identified patent and that said Letters Patent is hereby corrected as shown below:

Column 5,
Line 54, change the word "brier" to the word -- brim --.

Column 6,
Line 14, change the word "herein" to the word -- wherein --.
Line 22, change the word "m" to the word -- a --.

Signed and Sealed this

First Day of June, 2004

JON W. DUDAS
*Acting Director of the United States Patent and Trademark Office*